United States Patent [19]
Masuta et al.

[11] Patent Number: 5,910,444
[45] Date of Patent: Jun. 8, 1999

[54] PLANTS IN WHICH THE EXPRESSION OF S-ADENOSYLHOMOCYSTEINE HYDROLASE GENE IS INHIBITED

[75] Inventors: Chikara Masuta; Kyoko Uehara; Hideo Tanaka; Shigeru Kuwata, all of Yokohama, Japan

[73] Assignee: Japan Tobacco Inc., Tokyo, Japan

[21] Appl. No.: 08/669,536

[22] PCT Filed: Nov. 15, 1995

[86] PCT No.: PCT/JP95/02333

§ 371 Date: Jul. 12, 1996

§ 102(e) Date: Jul. 12, 1996

[87] PCT Pub. No.: WO96/14734

PCT Pub. Date: May 23, 1996

[30] Foreign Application Priority Data

Nov. 15, 1994 [JP] Japan ................................ 6-304200

[51] Int. Cl.⁶ .............................. A01H 4/00; C07H 21/00; C12N 5/14; C07K 14/415
[52] U.S. Cl. ........................ 435/419; 435/468; 800/278; 800/286; 800/298; 530/370; 536/24.5
[58] Field of Search ..................... 800/278, 286, 800/298; 530/370; 435/468, 419; 536/24.5

[56] References Cited

U.S. PATENT DOCUMENTS 5,107,065  4/1992  Shewmaker et al. .

FOREIGN PATENT DOCUMENTS 42-58292A  9/1992  Japan .

OTHER PUBLICATIONS

Liu et al, Antiviral Research, vol. 19, pp. 247–265 (1992).
Coulter–Karis et al, Ann. Hum. Genet., vol. 53, pp. 169–175 (1989).
Abel et al, Science, vol. 232, pp. 738–743 (May 9, 1986).
Harrison et al, Nature, vol. 328, pp. 799–801 (Aug. 27, 1987).
Gerlach et al, Nature, vol. 328, pp. 802–805 (Aug. 27, 1987).
Saito et al, Theor Appl Genet, vol. 83, pp. 679–683 (1992).
Cuozzo et al, Bio/Technology, vol. 6, pp. 549–557 (May 1988).
Golemboski et al, Proc. Natl. Acad. Sci. USA, vol. 87, pp. 6311–6315 (Aug. 1990).
Carr et al, Virology, vol. 199, pp. 439–447 (1994).
Zaitlin et al, Virology, vol. 201, pp. 200–205 (1994).
Schmülling et al, The EMBO Journal, vol. 7, No. 9, pp. 2621–2629 (1988).
Estruch et al, The EMBO Journal, vol. 10, No. 10, pp. 2889–2895 (1991).
Mitsui et al, Plant Cell Physiol., vol. 34, No. 7, pp. 1089–1096 (1993).
Masuta et al., *Proc. Natl. Acad. Sci. USA*, vol. 92, pp. 6117–6121 (Jun. 1995).
Report and Recommendations of the Panel to Assess the NIH Investment in Research on Gene Therapy, Dec. 7, 1995.
Gewirtz et al. PNAS USA, vol. 93, Apr. 1996, p. 3161–3163.
Fazio et al. Antiviral Research, vol. 13, 1990, p. 219–226.

*Primary Examiner*—Jeffrey Stucker
*Assistant Examiner*—Phuong T. Bui
*Attorney, Agent, or Firm*—Birch, Stewart, Kolasch & Birch, LLP

[57] ABSTRACT

The present invention discloses transgenic plants in which the expression of SAHH gene present in their genome is substantially inhibited. Such plants have excellent properties such as resistance to viruses.

6 Claims, 7 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1812 base pairs
      (B) TYPE: nucleic acid
      (C) STRANDEDNESS: single
      (D) TOPOLOGY: linear (ii) MOLECULE TYPE: cDNA to mRNA (xi) SEQUENCE DESCRIPTION: SEQ ID NO:1:

```
GAAGAGAAAA AAGCCTCTCA AATCTCATCT CTAACCACCC AATTTCTCAT ACTCGCTCTA      60

CCCATGGCTC TATTAGTCGA GAAGACCACC TCTGGCCGCG AGTACAAGGT CAAGGACATG     120

TCTCAGGCCG ATTTCGGCCG GCTTGAAATC GAGCTGGCCG AAGTTGAAAT GCCTGGTCTC     180

ATGGCTTGTC GTACTGAATT TGGCCCTTCA CAGCCATTTA AAGGTGCTAA GATTACTGGA     240

TCTTTACATA TGACCATTCA AACTGCAGTT TTGATTGAAA CCCTTACTGC TTTGGGTGCT     300

GAAGTTAGAT GGTGTTCTTG CAACATCTTC TCCACTCAAG ATCACGCCGC TGCTGCCATT     360

GCACGTGACA GCGCCGCCGT GTTCGCGTGG AAGGGTGAGA CTCTGCAGGA GTATTGGTGG     420

TGTACTGAGA GGGCACTTGA CTGGGGTCCA GGTGGTGGGC CCGACTTGAT CGTCGACGAT     480
```

```
GGTGGTGATG CTACACTCTT GATTCATGAG GGTGTTAAGG CAGAAGAAGA GTTTGCTAAG      540

AATGGGACAA TCCCAGATCC TAACTCTACC GATAATGCTG AGTTTCAGCT TGTACTTACT      600

ATTATTAAGG AAAGTTTGAA GACTGATCCT TTAAAATATA CCAAGATGAA GGAAAGACTC      660

GTCGGTGTTT CTGAGGAAAC TACCACTGGA GTTAAGAGGC TTTATCAGAT GCAGGCTAAT      720

GGAACTTTGC TTTTCCCTGC TATTAATGTT AATGATTCTG TTACCAAGAG CAAGTTCGAC      780

AACTTGTACG GATGCCGCCA CTCACTGCCC GATGGTCTCA TGAGGGCTAC TGATGTTATG      840

ATTGCCGGAA AGGTTGCCCT TGTTGCTGGT TATGGAGATG TCGGCAAGGG TTGTGCTGCT      900

GCCTTGAAAC AAGCCGGTGC CCGTGTGATT GTGACCGAGA TTGACCCTAT CTGTGCTCTC      960

CAGGCTACCA TGGAAGGCCT CCAGGTCCTT ACTCTAGAGG ATGTCGTTTC TGATGTTGAT     1020

ATCTTTGTCA CCACGACCGG TAACAAGGAC ATTATCATGG TTGACCACAT GAGGAAGATG     1080

AAGAACAATG CCATTGTTTG CAACATTGGT CACTTTGACA ACGAAATCGA CATGCTTGGT     1140

CTCGAGACCT ACCCTGGTGT CAAGAGGATC ACAATTAAGC CTCAAACCGA CAGATGGGTC     1200

TTCCCTGACA CCAACAGTGG CATCATTGTC TTGGCTGAGG GTCGTCTCAT GAACTTGGGA     1260

TGTGCCACAG GACACCCTAG TTTTGTGATG TCGTGCTCGT TCACTAACCA AGTCATTGCC     1320

CAACTCGAGT TGTGGAATGA AAAGAGCAGT GGGAAGTATG AGAAGAAAGT GTATGTCTTG     1380

CCAAAACACC TCGACGAGAA GGTTGCTGCA CTTCATCTCG GAAAGCTCGG AGCCAAGCTT     1440

ACCAAACTTT CGAAGGATCA AGCTGACTAC ATTAGCGTTC CAGTTGAGGG TCCTTACAAG     1500

CCTGCTCACT ACAGGTACTG AGCGAAAACA AATCGACAGA GGAGAACAGC ATTGTCGCGG     1560

CATGATTGTT TTGCATTTAA TACTTTGATT TTGTTTAGGA TACTAGTATT TTGAATATTG     1620

GTGGTGATAT ATTTGGGAGG AAGTGGCATG TTTTGCTGGA AAAGAAATGG GTCTTATTTG     1680

AAAGTAAGAC CAAAATGTGT TGAATAAGAT TATGGTTGGT GGTGTGATAT GATATTGTAG     1740

TAAGTTAGAA CCATTTGCTT TTTGGTGTAT GGTTTTTGTT TCAAGAAATC AAAGCAACAC     1800

TTTTACCTTT TC                                                        1812
```

(2) INFORMATION FOR SEQ ID NO:2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

```
GAAACACCCU GAGUCCNNNN GGACGAAACG GUCU                                   34
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

```
GGATAGTGGG ATTGTGCGTC                                                   20
```

(2) INFORMATION FOR SEQ ID NO:4:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GGATCTAACA GAACTCGCCG                                                       20
```

PLANTS IN WHICH THE EXPRESSION OF S-ADENOSYLHOMOCYSTEINE HYDROLASE GENE IS INHIBITED

Technical Field of the Invention

The present invention relates to transgenic organisms having various properties which are obtained by substantially inhibiting the expression of S-adenosylhomocysteine hydrolase (hereinafter referred to as "SAHH") genes with recombinant DNA techniques, as well as methods for creating such organisms.

BACKGROUND ART (Application to Plants)

The improvement of plants (introduction of desirable characters thereto) has been greatly dependent on classic breeding methods of crossing with wild species or mutants. Most of the varieties for use in the culture of ornamental plants and vegetables have been created through such efforts made by breeders. However, breeding often does not progress at all since a gene source does not exist. In addition, because breeding generally requires a long period of time even if a gene source exits, the improving of plants with genetic engineering techniques has been positively tried recently. For example, the creating a variety having resistance against viral diseases by conventional breeding methods is accompanied with many difficulties, e.g., an appropriate gene source cannot be found, or crossing with a wild species is difficult. In addition, with conventional breeding methods it is almost impossible to achieve drastic improvements, such as the creation of a dwarf plant or a dramatic increase in the number of flowers, and the like by regulating the subtle balance of plant hormones Recently, recombinant DNA techniques and plant tissue cultivation techniques have advanced and it has become possible to create virus-resistant plants and dwarf plants using such techniques. Major strategies so far tried are as described below.

(1) Creation of Virus-Resistant Plants

1) Introduction of a Viral Coat Protein Gene

In 1986, Powel Abel et al. (Science 232, 738) created a plant into which the coat protein gene of tobacco mosaic virus (TMV) had been introduced, and this plant was demonstrated to be TMV-resistant. Since then, a number of similar reports have been made throughout the world with various combinations of plants and viruses. However, a transgenic plant obtained by this method exhibits resistance against only one virus whose coat protein gene has been introduced (or extremely allied species thereof). In addition, the degree of resistance is greatly influenced by the inoculation concentration.

2) Use of a Satellite RNA

In some viruses, there is a low molecular weight RNA called satellite RNA. Satellite RNA depends on the parent virus for its replication and, in many cases, inhibits the growth of the parent virus to thereby remarkably reduce the symptoms induced by the virus.

By utilizing this property, it is possible to create a virus-resistant plant. To date, plants resistant to cucumber mosaic virus (Harrisson et al, Nature 328, 799) and tobacco ringspot virus (Gerlach et al., Nature 328, 802) have been created by introducing the cDNA of a satellite RNA into plants. In China, a plant integrating the cDNA of the cucumber mosaic virus satellite RNA has already been subjected to a field test to put it for practical use (Saito et al, Theor. Appl. Genet. 83, 679). However, this method is applicable to only those viruses having a satellite RNA.

3) Use of an Antisense RNA

A total or a partial cDNA of a virus is integrated into a plant so that it is transcribed and expressed in the antisense direction. When this plant is infected with the target virus, it is thought that the antisense RNA transcribed and the nucleic acid of the virus form a complex (a double-stranded RNA) to thereby inhibit the synthesis of viral proteins. As a result, the growth of the virus is inhibited. However, viral RNA is abudantly present in cells and has a complicated higher structure. Thus, the formation of such a complex is not considered easy and the effect of this method is not as great as expected (Cuozzo et al., Bio/Technology 6, 549). Even if resistance to viruses has been achieved, such resistance is expected only against the virus from which the cDNA was derived (or extremely allied species thereof), as observed in the method using a coat protein.

4) Use of a Ribozyme

A ribozyme is an RNA having an activity of self-catalyzed cleaving. It is possible to design a base sequence for a ribozyme so that it specifically cleaves viral RNA when the ribozyme is transcribed and expressed in plant cells. Similar to an antisense RNA, a ribozyme must form a complex with viral nucleic acid in order to produce its effect. Although there have not been many successful cases, for example, Edington et al. have reported that this method was effective when targeting at tobacco mosaic virus ("Viral Gene and Plant Pathogenesis").

5) Introduction of a Non-Structural Protein Gene

Recently, there have been reports on several viruses that a transgenic plant incorporating the total cDNA of a viral replication enzyme gene or the cDNA having a mutation exhibits a high resistance against viruses (Golemboski et al., Proc. Natl. Acad. USA 87, 6311; Carr et al., Virology 199, 439). However, there have been reported instances where the resistance obtained by this method is easily overcome by a virus of a different strain from that of the targeted virus (Zairlin et al., Virology 201, 200).

(2) Change of Plant Morphology by Varying an Endogenous Cytokinin Concentration

If plant morphogenesis can be artificially controlled, it is possible to improve a plant into a desirable morphology for humans. This is especially important for flower business. Recently, research concerning morphologenesis in higher plants has been rapidly advancing with molecular biological techniques.

The bacteria *Agrobacterium rhizogenes* which infects plants and induces hair root carries a giant plasmid called Ri plasmid. A part of this plasmid is integrated into a plant genome. It is reported that, when the three genes of rol A, B and C in Ri plasmid have been integrated separately in tobacco, various morphological changes are observed (Schmulling et al., EMBO J. 7, 2621). In particular, rol C has been found to be a gene which increases the amount of cytokinins, a kind of plant hormone (Estruch et al., EMBO J. 10, 2889). Transgenic plants created with this gene exhibit changes such as the shortening of internodes, the lowering of plant heights, extrusion of styles, an increase in the number of flowers, expedited flowering time and the like. Some enterprises have already been developing a rose variety with an increased number of flowers, a dwarf variety of prairie gentian, etc. utilizing rol C.

Recently, it has been reported that SAHH binds to cytokinins (a kind of plant hormone) in plants (Mitsui et al., Plant Cell Physiol. 34, 1089). SAHH is an enzyme which catalyzes the following reaction.

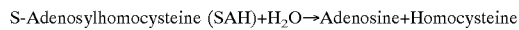

S-Adenosylhomocysteine (SAH)+$H_2O$→Adenosine+Homocysteine

Methylation in cells progresses in the presence of S-adenosylmethionine (SAM) as the methyl group donor irrespective of microorganisms, animals and plants. SAM, after supplying the methyl group, becomes SAH. Therefore, SAHH which is an enzyme that hydroylzes SAH controls the concentrations of SAM and SAH in living organisms. SAHH is a key enzyme playing an important role in the methylation reaction. Since there have been found some other proteins which bind to cytokinins, it is not clear whether SAHH is a receptor for cytokinins with which cytokinins directly exert their physiological activity. However, it is presumed that SAHH is deeply involved in the exertion of the physiological activity of cytokinins and that an endogeneous cytokinin concentration regulates the methylation reaction in which SAHH is involved. This is still a matter of conjecture, since the above-mentioned report provides no data on the effect resulted from the binding of SAHH to cytokinins. On the other hand, the results of Examples of the present invention suggest that the effect of the binding of SAHH to cytokinins is that SAHH concentration is regulates the concentration of endogenous cytokinins, as opposed to what is conjectured in the above article.

(Application to Animals)

Described below are materials currently used as therapeutic agents for viral diseases in order to inhibit the infection with or growth of animal viruses.

1) Vaccines

Vaccines are mainly preventive means to inactivate invaded viruses by utilizing antibody production by an animal's immune system against viral antigens. Recently, various vaccines have been improved making free use of rapidly advanced genetic engineering and protein engineering ("Molecular Virology Promoting Life Sciences", Ishihama et al. (eds.), 1992, Kyoritu Shuppan Co., Ltd.). Among viruses, however, there are a number of them which skillfully escape from the immune system and against which no vaccine is effective.

2) Interferons

Inferferons are proteins induced by a viral infection. Interferons not only act on peripheral cells to make them resistant to viruses, but also have divergent physiological activities. It is considered that interferons are one of cytokines. Although they have achieved some results in a clinical application as therapeutics for hepatitis C in Japan, their use is limited because of their serious side effects.

3) Nucleic Acid Analogues

Viral DNA/RNA synthetases and reverse transcriptases are inhibited by nucleic acid analogues. Those nucleic acid analogues which are put into actual use as anti-AIDS agents include dideoxythymidine (ddC), azidothymidine (AZT) and dideoxyinosine (ddI). They can be expected to exert great effects as medicines, but their side effects are also great in view of their modes of action.

4) Others

Research and development of antiviral agents today is focused upon antisense medicines and inhibitors against transcriptional control factors of viruses. Out of the former, a therapeutic agent developed by ISIS in the United States for treating viral diseases of the eyes induced by cytomegalovirus and herpes virus has already been tested clinically. The characteristic of antisense medicines is that one target is specifically aimed at. Other subjects of research include protease inhibitors which inhibit viral proteases.

5) SAHH Inhibitors

All of the antiviral agents so far described are targeted at viruses per se. However, for the inhibition of a virus continuously growing in cells, a considerable amount of an antiviral agent is necessary and yet counter-measures should also be taken to cope with possible mutation of the virus to escape from the agent or possible inactivation of the agent by the virus. On the other hand, there is an idea to inhibit viral growth by inhibiting enzymes in those cells which have been infected with the virus. One embodiment of this idea is an SAHH inhibitor, which induces methylation inhibition in cells by inhibiting the host cells' SAHH. As a result, the cap structure is inhibited to thereby inhibit the translational function of a target virus. Sufficient resistance to a virus has been confirmed in in vitro experiments at a concentration of SAHH inhibitors at which no phytotoxicity is observed (Wolfe et al, J. Med. Chem. 34, 2521). It is reported that SAHH inhibitors are particularly effective against (−) RNA viruses and double-stranded viruses and that they also inhibit some of (+) RNA viruses and DNA viruses. Recently, there have been reported that SAHH inhibitors are also effective against retroviruses such as HIV.

Problem for Solution by the Invention

As so far described, recombinant DNA techniques have been utilized for creating virus-resistant plants and dwarf plants and for treating viral diseases. However, as described above, there have been involved a number of problems.

It is an object of the invention to solve these problems and to provide organisms with various advantageous properties using recombinant DNA techniques.

Hereinbelow, the characteristics of the invention will be described briefly in comparison with prior art.

(Application to Plants)

(1) Creation of Virus-Resistant Plants

The resistance to viruses conferred by the present invention has a characteristic that prior art cannot achieve, i.e., effects can be expected against plurality of viral diseases. In the future, it will be possible to give plants a practical resistance to viruses by minimizing those negative influences caused by the inhibition of the expression an endogenous SAHH gene through changing the kind of a promoter, controlling the degree of antisense inhibition or the like.

(2) The Changing of Plant Morphology by Varying an Endogenous Cytokinin Concentration Morphological changes in plants induced by the invention (such as loss of apical bud dominance, dwarfing, extrusion of styles, immature pollen, increase in the number of flowers, expedited flowering time, suppression of aging, rooting from stems) are considered the results of influences upon the amount of endogenous cytokinins. These influences are similar to those of rol C described above, but the mechanism of influencing of the present invention is completely different from that of rol C. Furthermore, since it has been demonstrated, for example, that resistance to a wide variety of viruses is achieved mainly by the inhibition of methylation, the invention is recognized to have by far greater effects than those observed in rol C plants. In addition, considering that these effects are induced by antisense inhibition, there is a possibility that a completely opposite character may be induced through expression in the sense direction. For example, the suppression of lateral buds or the promotion of aging may be highly possible by devising an appropriate promoter. When the present invention is practiced by such antisense inhibition as described in Examples, the resultant transgenic plant does not produce any novel foreign protein and, thus, it will be advantageous to obtain public acceptance.

(Application to Animals)

When a resistance to viruses is conferred to cells by such antisense inhibition as described later in the Example of yeast, cytotoxicity, if observed any, is simply attributable to the specific inhibition of SAHH. On the other hand, when viral growth is suppressed by an SAHH inhibitor, there have been reported a number of cases where the inhibitor itself is metabolized to exhibit cytotoxicity in addition to the SAHH inhibition.

DISCLOSURE OF THE INVENTION

Figure 1:
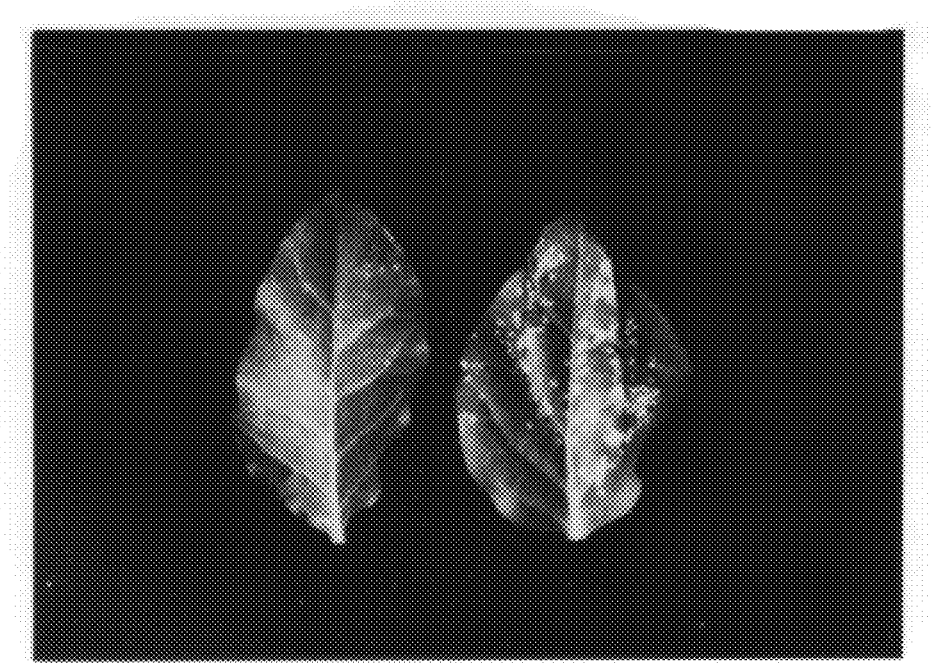
FIG. 1 is a photograph of the morphology of transgenic Xanthi nc tobacco. More specifically, it shows local lesions of the transgenic plant when inoculated with tobacco mosaic virus.

The present inventors have made extensive and intensive researches into methods for creating novel organisms using recombinant DNA techniques. As a result, the inventors have found that an organism having various excellent properties can be created by inhibiting the expression of SAHH genes present in the genomic DNA of the organism. Thus, the present invention has been achieved.

The invention relates to transgenic organisms in which the expression of SAHH genes present in their genomes is substantially inhibited by recombining a gene into their genomic genes, as well as methods for creating such organisms.

The present invention will be described below in more detail.

As an organism to be transformed by the invention, any organism may be used as long as the expression of SAHH gene can be inhibited in the organism. Target organisms include plants suffering great damage from plant viruses; plants into which introduction of a specific character (such as dwarfing, male sterility or increase in the number of flowers) is desired; or animals which need counter-measures against serious viral diseases. The invention aims at a wide range of organism species since, as described later, SAHH is present universally in organisms and yet differences in base sequences for SAHH genes are small among species. Specific examples of target organism species of the invention are as follows. In animals, experimental animals such as mouse and monkey may be enumerated. In plants, dicotyledonous plants such as tobacco, tomato, potato and rose may be enumerated as suitable plants. Monocotyledonous plants such as maize, rice and lily may also be used in the invention. Further, not only angiosperms but also gymnosperms may be target organisms of the invention.

Now, the gene or the property which is the characteristic of the transgenic organism of the present invention will be described below.

The transgenic organism of the present invention is characterized in that the expression of SAHH gene present in its genome is substantially inhibited. As a result of the inhibition of SAHH gene expression, the following changes will occur in the transgenic organism.

(1) Inhibition of Methylation Reaction

A number of reports have shown that the SAHH inhibitor described above exhibits an excellent growth inhibition effect against animal viruses (Wolfe et al., J. Med. Chem. 34, 2521). Inhibition of the methylation reaction at a concentration of the inhibitor at which animal cells do not undergo phytotoxicity suppresses viral growth sufficiently. It is believed a cap structure, which is extremely important for translation, is directly influenced by the methylation inhibition. The present invention has generated this phenomenon not through an inhibition by SAHH inhibitors but through the inhibition of expression of SAHH at the genetic level.

Thus, inhibition of methylation reaction confers animals and plants resistance to viruses. However, it is unknown as to whether the inhibition will influence upon other outside characters of transgenic organisms.

(2) Increase in the Amount of Endogenous Cytokinins

Figure 7:
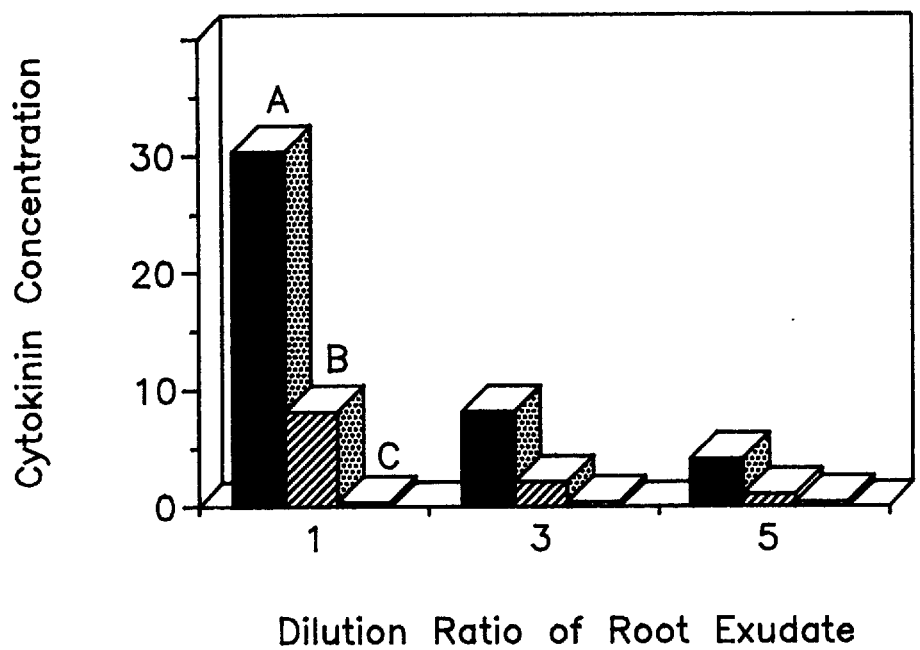
FIG. 7 is a graph showing endogeneous cytokinin contents in transgenic tobacco plants.

From the Examples of the invention, it has been confirmed that the amount of free, active cytokinins relatively increases by the inhibition of expression of SAHH which is also a cytokinin-binding protein (FIG. 7). Accordingly, it is considered that cytokinins are in an inactivated state through the binding to SAHH. Cytokinins regulated by the concentration of SAHH are plant hormones and thus even an extremely small change in their amount is believed to give great influences upon the morphology of a plant. Specifically, the following changes in character are expected.

1. Interactions with auxins (promotion of callus formation, growth of cells by enlargement, cell division or differentiation) For example, dwarfing, promotion of rooting, extrusion of styles, immature pollen, etc.
2. Loss of apical bud dominance (increase in lateral buds) For example, increase in the number of flowers as a result of increase in flower buds, increase in tillering, etc.
3. Prevention of aging (inhibition of chlorophyll decay) For example, enhancement of photosynthesis ability, retention of freshness of flowers, etc.
4. Opening of stomata (promotion of transpiration, promotion of photosynthesis)
5. Resistance to plant viruses With respect to the above-mentioned phenotypes of transgenic organisms, only those individuals which have acquired desirable characters may be selected from individuals having various properties.

On the other hand, character changes in transgenic animals are unknown because cytokinins, which are plant hormones, are not present in animals as functional molecules and because study of SAHH inhibitors still remains at the cellular level.

Now, the processes for creating the transgenic organism of the invention will be described.

The transgenic organism of the invention is created by recombining a gene into the genomic gene of the organism.

The term "recombining a gene into the genomic genes" used herein is intended to include all of the genetic engineering techniques exerted upon the genomic DNA of the target organism in order to substantially inhibit the expression of SAHH gene present in the genome.

Further, "to substantially inhibit the expression of SAHH gene" means to reduce such SAHH that actually functions in cells. This includes a method of inhibiting the transcription itself of mRNA, a method of trapping the transcribed mRNA, a method of synthesizing a protein which binds to SAHH, and the like. Preferable methods for substantially inhibiting the expression of SAHH gene are illustrated below.

(1) A method using antisense

This is a method wherein an antisense RNA against the base sequence for a target gene whose expression should be inhibited is expressed and this antisense RNA forms a double-stranded RNA with the target mRNA to thereby trap the target mRNA.

(2) A method using plus-sense

When a target gene is introduced into the genomic DNA in the plus-sense direction, usually the gene is over-expressed. However, on rare occasions, a decrease in the amount of the target mRNA is observed. This mechanism is not clear.

(3) A method using a ribozyme

A ribozyme is an RNA molecule 50 base pairs in size at the largest and has an antisense sequence against a target gene. The difference from the above-mentioned method using antisense is that the target mRNA is cleaved after the formation of a double-stranded RNA. Further, the ribozyme binds to the subsequent target to repeat cleaving.

(4) A method using a transcriptional control factor and a promoter region

This is a method to interfere the binding of the proteinous factor controlling the expression of a target gene to the DNA transcriptional control region (promoter). Concretely, the DNA sequence for the promoter is destroyed or the expression of the transcriptional control factor itself is inhibited.

(5) A method using a protein which binds to a target protein

The above-mentioned methods (1) to (4) are characterized in that the expression of a target gene is inhibited. On the other hand, this is a method to inactivate a target protein already expressed by expressing a protein which binds to it.

Among these methods, the method using antisense described in (2) above is preferable in the present invention.

Now, the methods (1) to (5) will be described specifically.

(1) A method using antisense

An SAHH antisense RNA means an RNA complementary to the base sequence for the mRNA transcribed from SAHH gene. This SAHH antisense RNA hybridizes to the target mRNA to form a double-stranded RNA. The mRNA trapped is no longer translated into a protein and is digested by a nuclease in cells.

An antisense RNA may be transcribed by simply linking SAHH gene to a vector in the reverse direction downstream of its promoter.

The SAHH gene used in the invention has already been disclosed by the present applicant (Japanese Unexamined Patent Publication No. 4-258292) and the base sequence for the gene is shown in SEQ ID NO: 1. As described earlier, SAHH is distributed widely in microorganisms, animals and plants and, particularly, it plays an important role in methylation reaction. To date, the following reports have been made on SAHH genes.

Human (Coulter-Karis et al., Ann. Hum. Genet. 53, 169), mouse (Ogawa et al., Proc. Natl. Acad. Sci. USA 84, 719), bacteria (Sgamga et al., Proc. Natl. Acad. Sci. USA 89, 6328), nematode (Genebank accession No. M64306), slime mold (Kasir et al., Biochem. Biophys. Res. Commun. 153, 359), Trypanosoma (Genebank accession No. M76556), tobacco (Japanese Unexamined Patent Publication No. 4-258292; Mitsui et al., Plant Cell Physiolo. 34, 1089), and Madagascar periwinkle (Schr[1] der et al., Plant Physiol. 104, 1099).

Base sequences for these genes and amino acid sequences encoded thereby are very well preserved beyond species (60–70%). This is comparable to the protein ubiquitin of which amino acid sequences are well preserved in all species of organisms.

An SAHH gene can be obtained, for example, by the method described below. First, a section from example, by the method floral axis is cultured on Murashige-skoog medium (flower bud-inducing medium) containing kinetin and indoleacetic acid. Then, mRNA is extracted from the resultant cultured tissue according to conventional methods and a cDNA library is prepared from the extracted mRNA. Subsequently, using mRNA extracted from an untreated tobacco floral axis and the mRNA obtained from the above cultured tissue, a cDNA probe labelled with a radioisotope such as $^{32}P$ is prepared separately.

These probes and the above cDNA library are subjected to hybridization. As a result of the hybridization, those cDNA clones are selected which do not hybridize to the probe from untreated floral axis but hybridize only to the probe from the cultured tissue. E. coli Jm109 containing the thus obtained SAHH gene was deposited at the National Institute of Bioscience and Human-Technology, Agency of Industrial Science and Technology (located at 1-3, Higashi 1-chome, Tsukuba City, Ibaragi Pref., Japan) as Tob-SAHH-1 under the accession No. FERM BP-4873 (date of deposit: Nov. 4, 1994). Thus, it is possible to obtain the SAHH gene from this microorganism.

A large number of expression promoters are known. They include those which are strong in transcriptional power and allow expression in every cell (such as 35S, 19S, nos); those which respond to light (such as rbc); those which respond to temperature (such as hsp); those which react with hormones and those which react tissue-specifically. When expression of the gene in a plant is intended, important points are as follows. Which effect of the present invention is expected; at which stage of growth the gene is expressed; and in which tissue the gene is expressed specifically. For example, in the case of conferring a resistance to plant viruses, preferably a promoter which allows expression of the gene in every cell, especially preferably a powerful promoter such as 35S is used. In the case of conferring male sterility to a plant in order not to give influences upon characters of other plants, a flower-specific promoter is preferably used. For animals, animal virus-derived promoters are mainly known as powerful promoters (e.g., SV40 early, SV40 late, MMTV-LTR and SVLTR). In the case of conferring a resistance to viruses by SAHH antisense inhibition at the cellular level, these powerful promoters are preferably used.

With respect to the gene to be inserted in the antisense direction, any gene which codes for SAHH may be used without particular limitation since SAHH has 60 to 70% homology at the nucleic acid level beyond species. It is considered that the higher the degree of relatedness between the organism species to be transformed and the original source organism of the SAHH gene to be inserted in the antisense direction is, the more intense the antisense inhibition becomes. On the contrary, it is considered that the lower the degree of relatedness between the two organisms, the weaker the antisense inhibition becomes. In addition, the SAHH gene to be inserted in the antisense direction is not necessarily a whole gene. Generally, it is considered that a higher degree of antisense inhibition will be achieved when a whole gene is inserted; however, there may be cases where sufficient effects are obtained even when a part of the gene has been inserted. It should be noted, however, that preferably a DNA fragment containing the AUG at the translation start site is used.

The selection of an expression vector for transforming animals an plants may vary depending on whether the target gene is to be expressed at the cellular or individual level. A vector has been created which is the same in the basic structure (gene cassette) placing the target gene between a promoter and a terminator but which is provided with base sequences necessary for the incorporation of the target gene into the host DNA outside the gene cassette. For example, in plant vectors, the RB (right border) and LB (left border) of a vector used in an Agrobacterium-mediated method are such base sequences. In animal vectors, the LTR (long terminal repeat) of a retrovirus vector is one example of such a base sequence.

The transfer of an antisense SAHH gene into a host organism does not require a special method. In plants, this transfer may be performed, for example, by the leaf disk technique using Agrobacterium. In animals, the transfer may be performed by the liposome method, electroporation, microinjection or the like. When the leaf disk technique is used, a transgenic plant can be obtained by the following procedures. An antisense SAHH gene is inserted into an appropriate plant expression vector, which is then transferred into Agrobacterium. Subsequently, leaf disks cut from germ-free leaf of a target plant are soaked in the culture solution of the above Agrobacterium to form calluses. A transgenic plant can be obtained by selecting only those individuals which have been transformed. This selection may be performed by adding an appropriate antibiotic to the medium on which calluses are to be formed and judging from the presence or absence of a resistance to the antibiotic. A method of transformation using Agrobacterium is said applicable to only dicotyledonous plants such as tobacco and not applicable to monocotyledonous plants (De Cleene M. 1976; Bot. Rev. 42:389–466). However, according to the procedures described in the International Patent Publication No. WO 94/00977 and Japanese Patent Application No. 6-27320 filed previously by the present applicant, the above method is also applicable to monocotyledonous plants. Briefly, it becomes possible to transform monocotyledonous plants by soaking a cultured tissue which is in the process of dedifferentiation or after dedifferentiation in the culture solution of an Agrobacterium. Further, when the target plant is a tree, it is also possible to transform it according to conventional methods. In trees such as pine, poplar and eucalyptus, a method of transformation has been already established as a stable technology. In other trees, it is also possible to transfer an SAHH gene by suitably arranging conditions for tissue culture and devising a method of transformation. For tissue culture of trees, detailed description is found on pages 60–73 in "Plant Biotechnology II" (published by Tokyo Kagaku Dojin Co. Ltd.). A method of transforming poplar using Agrobacterium is reported, for example, in Confalonieri et al., "Plant Cell Report 13" 256–261 (1994).

(2) A method using plus-sense (homologous recombination)

All or a part of an SAHH gene is integrated into a plant or animal expression vector in the original base sequence so that it is transcribed to mRNA. The obtainment of an SAHH gene and the selection of a promoter are as described in (1) above. The probability of achieving the inhibition of SAHH expression according to this method is thought considerably low, but not zero. The mechanism is unclear but homologous recombination can be considered. If this assumption is correct, the base sequence introduced is significant and the transcription from the promoter has nothing to do with the inhibition.

Anyway, the present invention includes the destruction of SAHH genes by homologous recombination. Now, specifically illustrated below is a case of transforming a plant at the individual level so that a plus-sense SAHH is expressed. First, a commercial plant expression vector pBI121 (Toyobo) is digested with appropriate restriction enzymes to remove GUS gene. For example, the vector is co-digested with SmaI and SstI. Then, an SAHH gene cloned at the EcoRI site of a commercial plasmid p Bluescript SK+ (Toyobo) is cut out with SmaI and SstI so that the same cohesive ends are generated. At this time, it is confirmed that the cohesive end produced by SmaI comes on the '5 end side of the SAHH gene and that neither SmaI site nor SstI site exists in the SAHH gene. According to the manual of a commercial ligation kit (Takara Shuzo), the SAHH fragment is linked to the vector. Then, E. coli (such as JM109) is transformed with the vector to thereby obtain a recombinant plasmid. This plasmid is amplified by conventional methods, recovered and used for transforming a plant. With respect to a method of transformation, plants may be transformed by the leaf disk technique or the like and animals by the liposome method, electroporation, microinjection and the like, as described in (1) above.

(3) A method using a ribozyme

Figure 8:
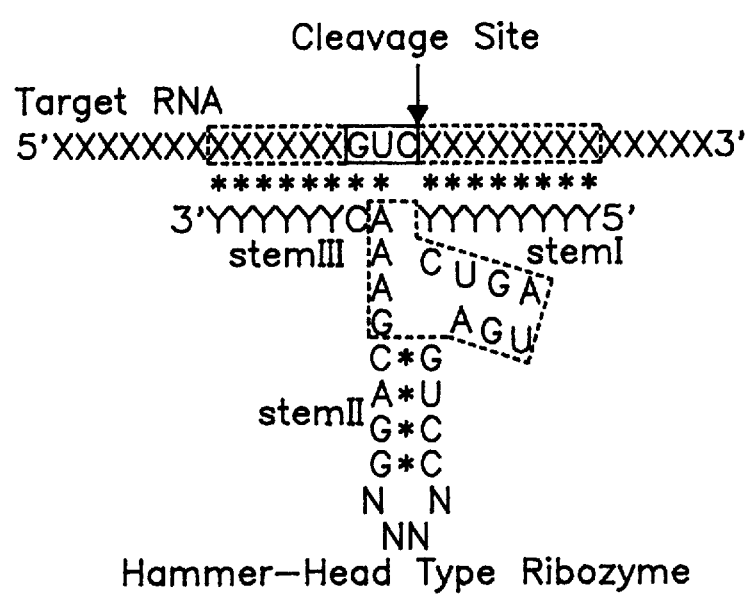
FIG. 8 is an illustration of a hammer-head type ribozyme used in the present invention.

A ribozyme is an RNA molecule 50 base pairs in size at the largest. It is composed of a portion containing a complementary strand sequence to bind to a target SAHH RNA, a portion of preserved sequence necessary for cleaving RNA, and a portion to form a higher structure (such as hairpin type and hammer-head type). First, a base sequence is designed so that the sequence will bind to the mRNA of the SAHH gene to be used (the target RNA) and cleave it. Then, a DNA fragment having this base sequence is synthesized. Subsequently, the DNA fragment is linked to a promoter in a plant or animal expression vector as described in (1) above and integrated into the genomic DNA of an organism to be transformed. For researches into SAHH inhibition in animals at the cellular level, ribozymes may be used as described below. DNA derived from a ribozyme is cloned downstream of a promoter (such as T7, T3 and SP6) of a common transcription vector to synthesize ribozyme molecules abundantly in an in vitro transcription system. Cells are allowed to directly take in these molecules. It is also technically possible to chemically synthesize a ribozyme. At this time, if a ribozyme is synthesized using a nucleotide derivative which will make the ribozyme nuclease-tolerant, the effect are expected to become greater. Hereinbelow, the procedures to knockout the SAHH gene in a plant individual by this method will be described specifically. For example, when the cleaving of the mRNA of the SAHH gene with a hammer-head type ribozyme is planned, first the ribozyme is designed targeting on GUC in the mRNA of the target SAHH gene. This method of designing is introduced in detail on pages 83–88 in "JIKKENN IGAKU (Experimental Medicine)" vol. 12. Briefly, a target site is determined to that a secondary structure as shown in FIG. 8 is formed. The lengths of stem I and stem II are preferably 7–10 bases, respectively. If the target site is the GUC at positions 660–663 in the base sequence for the tobacco SAHH gene shown in SEQ ID NO: 1, the following ribozyme may be designed.

5'GAAACACCCUGAGUCCNNNGGAC-
GAAACGGUCU3' (SEQ ID NO:2) (N may be any base)

When the ribozyme has been designed, a DNA sequence containing the ribozyme sequence is synthesized as two oligonucleotides of a sense strand and an antisense strand with a DNA synthesizer. At this time, it is preferable to add to the 5' end an appropriate restriction site since the DNA sequence is to be integrated into a vector afterward. The DNA synthesis may be performed with a commercial DNA synthesizer such as an ABI DNA synthesizer Model 380A. These two DNAs are mixed and annealed to thereby form a double-stranded DNA. After digestion with a restriction enzyme, the double-stranded DNA is cloned, for example, downstream of 35S promoter in pBI121. The resultant recombinant plasmid is used to transform a plant. The transformation at this stage may also be performed by the leaf disk technique using Agrobacterium or the like for plants and by the liposome method, electroporation, microinjection or the like for animals, as described in (1) and (2) above. The ribozyme designed in this section is one example and the cleaving of the SAHH mRNA may be carried out at a different site.

(4) A method using a transcriptional control factor and a promoter region

A. A method using a promoter region

First, the genomic genes of a target organism are separated from each other and the promoter region controlling the transcription of the SAHH gene is specified. In the case of tobacco, a genomic library is prepared using λ phage vector EMBL3 (Stratagene) or the like. The library is screened using as a probe a CDNA clone of an SAHH gene which has been isotope-labelled with a commercial random primary labelling kit (Takara Shuzo). The method for preparing this library and the method for screening are as described in detail in Japanese Patent Publication No. 5-236964. Briefly, epithelial cells of tobacco floral axis are cultured on Murashige-Skoog medium containing kinetin, indoleacetic acid, sucrose, thiamine hydrochloride and myo-inositol. Then, total RNA is extracted from the tissue section. Subsequently, poly (A) RNA is collected using an oligo-dT column and a CDNA library is prepared from this poly (A) RNA. A CDNA probe is prepared separately from poly (A) RNA obtained from the above cultured tissue and from poly (A) RNA extracted from an untreated tobacco floral axis. Then, those clones are selected from the above CDNA library which hybridize only to the probe from the cultured tissue but do not hybridize to the probe from untreated tissue.

The base sequence for the resultant genomic clone is determined by conventional methods (e.g., with a DNA sequencer manufactured by ABI) and the promoter region is specified. If this promoter region is destroyed with the homologous recombination technique or the like, the transcription of the SAHH gene will be completely stopped. The homologous recombination technique is also called gene targeting. This is a technique utilizing the phenomenon that, when the same base sequence as the target sequence to be destroyed has been integrated into DNA, a recombination occurs accidentally at the time of replication of the DNA. Specifically, the target promoter region is incorporated in the genomic DNA by the method described in (2) above.

B. A method using a transcriptional control factor

First, the presence of a protein which binds to the promoter region is confirmed by the gel shift assay (gel retardation assay) or the like and then the protein (transcription factor) is purified by column chromatography. From the purified protein, a probe for detecting the gene coding for this protein is prepared. Then, the gene is separated using this probe. Finally, using the separated gene fragment, the expression of the transcription factor protein is inhibited.

The purification of a transcription factor protein may be performed, for example, according to the procedures described in the experimental examples on pages 83–109 in "Laboratory Manual: Functional Analysis of Plant Genes" (published by Maruzen Co., Ltd.).

Briefly, first, the nuclear fraction is isolated from a tissue of the target plant by centrifugation. To this fraction, NaCl is added to extract nuclear proteins. The resultant mixture is centrifuged at 25000×g for 30 minutes and the supernatant is recovered. This supernatant is dialyzed in a dialysis buffer to thereby obtain a nuclear extract. Thereafter, a DNA fragment containing the promoter region of the SAHH gene is recovered from a gel by electrophoresis. One end of the DNA fragment is labelled with [$\gamma$-$^{32}$ $^P$]ATP and polynucleotide kinase. The above-mentioned nuclear extract and the labelled DNA are mixed and incubated at room temperature for 30 minutes. The reaction product is subjected to electrophoresis using 5% polyacrylamide gel. The resultant gel is transferred to a filter pater, dried and then subjected to autoradiography. If a gel shift is observed, this means the presence of a DNA-binding protein. For the purification of this protein, various techniques and methods may be used. For example, salting out (such as ammonium sulfate salting out) utilizing difference in solubility, fractionation with an organic solvent (such as acetone and ethanol), separation methods utilizing a molecular size (such as ultracentrifugation, gel filtration), immunological methods and the like may be used. The DNA-binding protein is partially purified by a combination of column chromatographies (e.g., ion exchange, hydrophobic or affinity chromatography and the like). The kind of column chromatography to be used is determined by the nature of the target protein. It is necessary to establish the optimum conditions in advance by conducting a small-scale preliminary experiment using a portion of the sample.

As a method for preparing the above-mentioned probe, there are a method wherein the sequence which binds to the promoter protein is determined by the DNAseI footprinting or the like, and an oligonucleotide having the sequence is synthetized to thereby obtain a probe; a method wherein the above DNA-binding protein is purified and a probe is prepared from the amino acid sequence of the protein; and the like. The second method may be carried out as follows, for example. A portion of the amino acid sequence for the protein is determined with an ABI protein sequencer or the like according to the operation manual thereof. Then, based on this information, the base sequence for the gene is estimated. At the same time, an mRNA is prepared from a tissue expressing SAHH well and a cDNA library is prepared therefrom in advance. The method for preparing a cDNA library is as described in Japanese Unexamined Patent Publication No. 4-258292. Briefly, a section from the epithelium of tobacco floral axis is cultured on Murashige-Skoog medium containing kinetin and indoleacetic acid. Then, total RNA is extracted from the cultured tissue. Subsequently, poly (A) RNA is collected from the RNA using an oligo-dT column. From this poly (A) RNA, cDNA is synthesized and a cDNA library is prepared. A portion of genes is amplified by PCR and a probe is prepared from the DNA fragment obtained, or an oligonucleotide probe is prepared. The above-mentioned library is screened using the probe. A standard PCR is as follows. Based on the information on the amino acid sequence, base sequences for the 5' and the 3'end portions (for the 3' end sequence, a complementary strand) are estimated from amino acid codons and a primer mixture is synthesized in such a manner that produces as less combinations as possible. Addition of a restriction site to the primers will be convenient for the subsequent cloning. Tobacco DNA (2 µg) and the two primers described above are mixed and denatured by boiling 2 minutes or the like. To the resultant mixture, a buffer, a polymerase and so forth are added to thereby obtain a reaction solution. Generally, this reaction solution is composed of 67 mM Tris-HCl buffer (pH 8.8), 16.6 mM ammonium sulfate, 6.7 mM magnesium chloride, 10 mM mercaptoethanol, 200 mM dNTPs, 1 µg of each primer, and 5 units of Taq polymerase (Takara Shuzo). Such a reaction solution is heated with a DNA thermal cycler (Takara Shuzo) at 92° C. for 1.5 minutes, then left stationary at 45° C. for 2.5 minutes and further reacted at 72° C. for 3 minutes. These operations make one cycle and this is repeated 25 times. The amplified DNA fragment is recovered by agarose gel electrophoresis. Then, it is labelled with an isotope and used as a probe, as described above. On the other hand, the isotope-labelling of an oligonucleotide is performed by conventional methods; it can be performed easily using, for example, Takara Shuzo mega label kit.

The DNAseI footprinting is a method used to identify a binding region for a nuclear protein. The contents of this method is described in detail in "Laboratory Manual: Functional Analysis of Plant Genes" (published by Maruzen Co., Ltd.) supra. Briefly, first, a DNA fragment of which one of the ends is labelled with $^{32}P$ and a nuclear extract are mixed and partially digested with an appropriate amount of DNaseI. Then, a partially digested DNA sample is subjected to electrophoresis using a denatured polyacrylamide gel and autoradiography. As a result, a band showing a ladder-like shape by each base is obtained. Since the region to which a protein has specifically bound is protected from the cleavage by DNaseI, the band at this region becomes weaker than the other regions or completely disappears. By simultaneously running a sample for base sequence determination in the electrophoresis, it is possible to estimate the binding region of the protein.

A method for inhibiting the gene of transcription factor protein is preferably selected from those described in (1) to (3) above. Particularly preferable is the antisense method described in (2) in view of the simplicity in its technology.
(5) A method using a protein which binds to the target protein At present, it is not clear if there exists a protein which binds to SAHH. First, SAHH is labelled, mixed with an extract from an animal or plant tissue and left stationary. Then, the presence of a binding protein is examined by the gel shift assay. If there exists a binding protein, the protein is purified and the gene thereof is obtained as described in (4) above. This gene is incorporated downstream of the promoter in an expression vector so that it is expressed in the sense direction. The target organism is transformed with this vector. The transformation here may also be performed by the leaf disk technique using Agrobacterium or the like in plants and by the liposome method, electroporation, micro-injection or the like in animals, as described above. The resultant transgenic organism produces the SAHH-binding protein excessively to thereby inhibit the activity of SAHH. When an SAHH-binding protein has not been obtained easily, the gene of an SAHH antibody may be used. First, a mouse is immunized by injecting SAHH several times and then its spleen is removed. The immunization of a mouse and the collection of spleen cells may be performed by known methods such as those described on pages 148 to 151 in "Biotechnology Experiment Manual" (published by Sankyo Shuppan Co., Ltd.). If a hybridoma of a monoclonal antibody is obtainable, it may be used. mRNA is prepared and using, for example, a commercial kit manufactured by Pharmacia (Recombinant Phage Antibody System), the gene of a recombinant antibody is obtained. According to the manual, the target gene can be easily obtained. This gene is incorporated downstream of the promoter in an expression vector in the sense direction so that the gene is overexpressed in cells. The target organism is transformed with this vector. The transformation here may be performed by a method similar to those described above.

Best Modes for Carrying Out the Invention

The present invention will be described more specifically below with reference to Examples, which should not be construed as limiting the scope of the present invention.

[EXAMPLE 1]

Creation of Transgenic Tobacco
[1] Summary of the Experimental Results

An SAHH gene isolated from tobacco was linked to a plant expression vector downstream of its 35S promoter so that the gene is expressed in the antisense direction in every cell. This recombinant DNA was introduced into the genome of tobacco by the transformation method using Agrobacterium. More than 100 individuals of the resultant transgenic tobacco were analyzed. Further, in order to confirm that each of the characters of the transgenic tobacco are inherited to subsequent generations, those individuals which were obtained from R1 seeds produced by selfing or artificial crossing. Major changes in character observed are described below. Most of these changes were as expected from the principle described earlier in the section titled "Means to solve the Problem".
(1) Resistance to a plurality of viruses (FIG. 1, Tables 3 and 4),
(2) Dwarf plants (FIGS. 2 and 3), (3) Increase in the number of lateral buds (FIGS. 2 and 4), (4) Increase in the number of flowers (Table 1), (5) Flowering time is expedited (7–10 days), (6) Inhibition of aging (FIGS. 2 and 3), (7) Male sterility (FIG. 5), (8) Change in flower color (white-red).

The finding that the expression inhibition of SAHH gene by antisense inhibition is associated with resistance to plant viruses was made receiving a hint from the fact that SAHH inhibitors positively studied in the field of animal viruses toward the use as antiviral agents. The present invention of which the effect has been proved in plant viruses is believed easily applicable to animal viruses. Therefore, the expression inhibition of SAHH at the genetic level according to the invention is not limited to plants.

Experimental methods and procedures will be described below for each item.
[2] Preparation of a CDNA Library A section from the floral axis epithelium of tobacco (*Nicotiana tabacum* BY-4) was cultured on Murashige-Skoog agar medium containing kinetin (1 µM) and indoleacetic acid (1 µM) for one day. Ten grams of the resultant cultured tissue was crushed in 20 ml of an extraction buffer (4M guanidine thiocyanate, 5 mM sodium citrate, 0.5% Sarkosyl, 2 mM β-mercaptoethanol) with a Polytron homogenizer. The resultant solution was centrifuged at 4000×g for 20 minutes and the supernatant was recovered.

This supernatant was over-layered upon 4 ml of 5.7M cesium chloride solution placed in a centrifuge tube and centrifuged at 28000 rpm for 20 hours. Then, the supernatant was discarded and the precipitate was recovered. This precipitate was dissolved in 1 ml of a buffer (10 mM Tris-HCl, 1 mM EDTA, 0.1% SDS). To the resultant solution, an equal volume of a mixture containing phenol:chloroform: isoamyl alcohol (25:24:1) was added, mixed well and centrifuged to thereby recover the aqueous phase of the upper layer. To the resultant aqueous phase, 5M sodium chloride was added to give a concentration of 0.25M. Further, 2.5 volumes of ethanol was added thereto and left stationary at −20° C. overnight. Then, the solution was centrifuged at 10,000×g for 20 minutes and the precipitate obtained was washed with 70% ethanol and dried under reduced pressure.

The resultant dried, standard product was dissolved in 500 ul of TE buffer (10 mM Tris-HCl, 1 mM EDTA) to thereby obtain a solution of the total RNA. This RNA solution was treated at 65° C. for 5 minutes and then quickly cooled on ice. To this solution, sodium chloride was added to give a concentration of 0.5M and poured into an oligo-dT cellulose column pre-equilibrated with TE buffer. Then, the column was washed with about 10 volumes of a buffer (0.5M NaCl, 10 mM Tris-HCl, 1 mM EDTA). Thereafter, poly(A)+ RNA was eluted with TE buffer.

To the resultant eluate, 1/10 volume of 5M sodium chloride solution and 2.5 volumes of ethanol were added, mixed and left stationary at −70° C. Then, the solution was centrifuged at 10,000×g.

The resultant precipitate was washed with 70% ethanol and dried, to thereby obtain 10 ug of poly(A)+ RNA. This poly(A)+ RNA was dissolved in 10 ul of water and 2 ul of the resultant solution was used to prepare a cDNA library. The preparation of this cDNA library was carried out using λgt11 cDNA synthesis system and a cDNA cloning system both manufactured by Amersham and according to the manufacturer's protocols.

[3] The Screening of the Library

Two micrograms of the poly(A)+ RNA obtained from the above-described cultured tissue and 10 ul of [α-$^{32}$P] dCTP (3000 Ci/mmol, 10 µCi/ul) were reacted at 37° C. for one hour in 30 ul of a reaction solution [50 mM Tris-HCl (pH 7.6), 2 mM DTT, 5 mM MgCl$_2$, 40 mM KCl, 1 mM dGTP, dATP and dTTP, 5 uM dCTP, 20 units of human placenta RNAse inhibitor, 2 ug of oligo-dT primer, 40 units of reverse transcriptase], to thereby prepare a cDNA probe.

In a similar manner, a cDNA probe was prepared from poly(A)+ RNA extracted from an untreated floral axis.

Subsequently, the phage which was constituting the above cDNA library was allowed to infect E. coli and to propagate on LB agar medium. DNA from about 1400 phages was transferred to two nylon membranes separately.

The nylon membrane to which the phage DNA had been transferred and the CDNA probe prepared above were hybridized in a solution containing 6×SSC (0.9M sodium chloride, 0.09M sodium citrate), 0.1% SDS, 5×Denhart's solution (0.1% Ficoll, 0.1% polyvinyl pyrrolidone, 0. 1% bovine serum albumin) and 50 ug/ml of denatured salmon sperm DNA at 65° C. for 20 hours. Then, the membrane was taken out and washed with a solution containing 2×SSC and 0.5% SDS at 65° C. for one hour. After this membrane was dried, an X ray film was adhered thereto and exposed.

As a result, 10 clones could be selected which only hybridized to the probe from the cultured tissue but did not hybridize to the probe from the untreated floral axis. One of these clones was closely analyzed and it was found that the insert of this clone was small about 300 base pairs in size. Then, in order to obtain a clone having a longer insert, the cDNA library was further screened using the insert of this clone as a probe.

As a result of this screening, a clone having an insert of about 1.8 K base pairs. The insert of this clone was subcloned into a plasmid vector (Bluescript manufactured by Stratagene) and its base sequence was determined by the dideoxy method. The base sequence for the insert thus decided is shown as SEQ ID NO: 1. The length of this insert is 1812 base pairs.

[4] The Cloning of a Gene into a Plant Expression Vector and Transformation of Plants Tobacco SAHH gene was inserted into a plant expression vector, pBI121 (Toyobo), at the SmaI-SacI site so that it is expressed in the antisense direction. Using the recombinant plasmid obtained, two varieties of tobacco (Nicotiana tabacum L. cv. BY-4 and N. tabacum L. cv. Xanthi nc) were transformed by the leaf disk technique using Agrobacterium. (Hereinafter, the transgenic BY-4 tobacco and the transgenic Xanthi nc tobacco are sometimes abbreviated to "SHB" and "SHX", respectively.) In this Example, the method described on pages 164–165 in "Plant Biotechnology II" (Yasuyuki Yamada & Yoshimi Okada (eds.), 1991, Tokyo Kagaku Dojin Co., Ltd.) was employed. Briefly, tobacco leaf disks were sterilized and soaked in a suspension of Agrobacterium tumefaciens (LBA4404) which had been allowed to acquire the target plasmid by the freeze-thawing method for about 30 seconds to thereby inoculate the bacterium. The leaf disks were infected with the bacterium by culturing for about two days in a medium containing no antibiotics. Then, the leaf disks were washed and placed on a medium containing antibiotics to thereby select transformants. Transformed calluses were selected with Murashige-Skoog medium containing kanamycin (100 µg/ml) and claforan (250 µg/ml). The transformants were bred at 25° C. under 16 hour lighting. Those which exhibited shooting were transferred to a rooting medium to induce rooting. Thereafter, the individuals were potted. As a rooting medium, Murashige-Skoog medium was used. In most of the potted individuals, lateral buds were formed so vigorously that herbaceous cutting of clone individuals could be easily performed. Further, most of those individuals were dwarfed, showing shorter internodes compared to non-transgenic individuals. This tendency was particularly strong in BY-4. There were observed several transgenic BY-individuals which had almost no stem and came into flower, remaining in a rossette-like shape. Generally, flowering was seen about one week earlier and the number of flowers increased two to three times. Flowers of various colors were observed including those of light pink (the original color of tobacco flower), red with uncolored spots and dark red.

Hereinbelow, the characteristics of those transgenic tobacco plants in appearance will be described below with reference to figures and tables.

Figure 2:
FIG. 2 is a photograph of the morphology of transgenic Xanthi nc tobacco showing the appearance thereof.

FIG. 2 shows the appearance of transgenic Xanthi nc tobacco before flowering. The plants at the center and at the left are transgenic plants. They have more lateral buds and darker green leaves compared to the non-transgenic plant shown at the right.

Figure 3A:
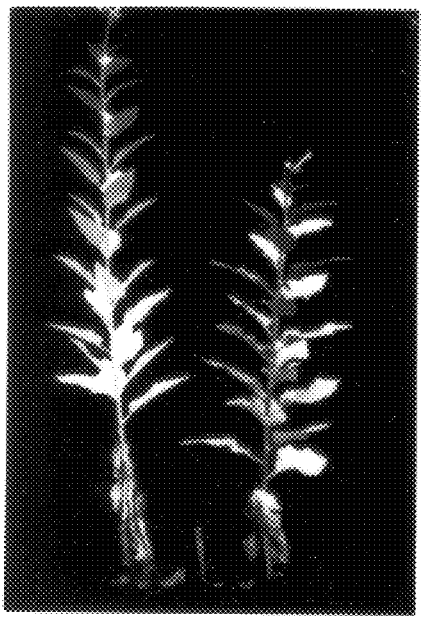
FIGS. 3A and 3B are photographs of the morphology of transgenic Xanthi nc tobacco showing the appearance of the plant coming into flower.
Figure 3B:

FIG. 3 shows the appearances of a transgenic Xanthi nc tobacco plant (FIG. 3A) and a transgenic BY-4 tobacco plant (FIG. 3B) both flowering. In both photographs, the plant at the right exhibiting shorter internodes and dwarfing is a transgenic plant.

Figure 4:
FIG. 4 is a photograph of the morphology of transgenic Xanthi nc tobacco showing an individual having an abnormally large number of lateral buds and a large number of flowers.

FIG. 4 shows a transgenic Xanthi nc tobacco plant having an abnormally large number of lateral buds and a number of flowers.

Figure 5A:
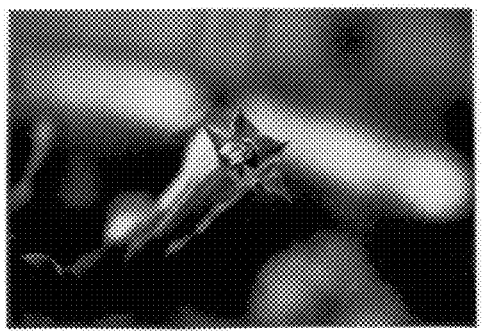
FIGS. 5A and 5B are photographs of the morphology of transgenic Xanthi nc tobacco showing a floral portion thereof.
Figure 5B:

FIGS. 5A and 5B show portions of a flower of a transgenic Xanthi nc tobacco plant. In about one third of the transgenic individuals, extrusion of the stigma from the flower (male sterility) was observed. The pollen of these individuals is immature and extremely low in germination ability.

Table 1 shows the number of flowers in transgenic Xanthi nc tobacco plants. The figures shown in the table are mean values for 10 individuals measured. Since one third of the transgenic individuals do not have fertility as described above, such individuals were excluded from the counting of the number of seed capsules.

TABLE 1

The Number of Flowers and the Number of Seed Capsules in Transgenic Individuals

| Plant | Number of Flowers | Number of Seed Capsules |
|---|---|---|
| SHX ($R_0$) | 31.1 ± 6.7 | 25.1 ± 4.5 |
| Control | 17.2 ± 4.5 | 13.5 ± 2.4 |

Table 2 shows a summary of detailed observation of 20 individuals each of transgenic tobacco plants BY-4 and Xanthi nc on the degree of dwarfing, the number of lateral buds and the degree of stigma extrusion.

TABLE 2

Phenotypes of Transgenic Tobacco Plants

| Index | Phenotype | Xanthi nc (N = 20) | BY-4 (N = 20) |
|---|---|---|---|
| | Stigma extrusion | | |
| 1 | Style has the same length as that of stamens or is shorter than stamens. | 13 | 9 |
| 2 | Style is somewhat longer than stamens. | 2 | 3 |
| 3 | Style is clearly longer than stamens. | 3 | 5 |
| 4 | Stigma is extruding from petals. | 2 | 2 |
| | Average index: | 1.7 | 2.1 |
| | Dwarfing | | |
| 1 | Height is the same as that of non-transgenic individuals. | 4 | 3 |
| 2 | Somewhat dwarfed. | 14 | 8 |
| 3 | Height is less than one half of that of non-transgenic individuals. | 2 | 5 |
| 4 | Height is less than 1/10 of that of non-transgenic individuals. | 0 | 4 |
| | Average index: | 1.9 | 2.5 |
| | Lateral buds | | |
| 1 | The number of lateral buds is the same as that of non-transgenic individuals. | 0 | 0 |
| 2 | Formation of non-elongating lateral buds. | 3 | 3 |
| 3 | More lateral buds than seen in non-transgenic individuals | 15 | 12 |
| 4 | Witches' broom | 2 | 5 |
| | Average index: | 3.0 | 3.1 |

[EXAMPLE 2]

Creation of Transgenic Petunia

[1] The Cloning of a Gene into an Expression Vector and Transformation of Plants In a manner similar to that described in Example 1, Tobacco SAHH gene was inserted into a plant expression vector pBI121 so that the gene is expressed in the antisense direction. Using the resultant recombinant plasmid, petunia (varieties: H1 and No. 22) was transformed. Like in Example 1, the transformation was carried out by the leaf disk technique. During this process, acetosyringone was added to the medium for coculture to give a concentration of 100 μm in order to promote the infection of petunia leaves with Agrobacterium. The selection and redifferentiation of transformants and the like were also carried out in a manner similar to that described in Example 1. However, the salt concentration of the rooting medium was reduced to ½ of the salt concentration of Murashige-Skoog medium.

[2] Detection of a DNA Fragment having the 35S Promoter Sequence

To confirm that the target DNA was integrated into the resultant transgenic petunia, the 35S promoter region was amplified by PCR. The sequences for the primers and the conditions employed were as follows.

3' end primer: GGATAGTGGGATTGTGCGTC (SEQ ID NO:3), 5' end primer: GGATCTAACAGAACTCGCCG (SEQ ID NO:4). One cycle consisted of three steps of at 94° C. for 2 minutes, at 65° C. for 30 seconds and at 72° C. for 2 minutes. This cycle was repeated 25 times.

Figure 9:
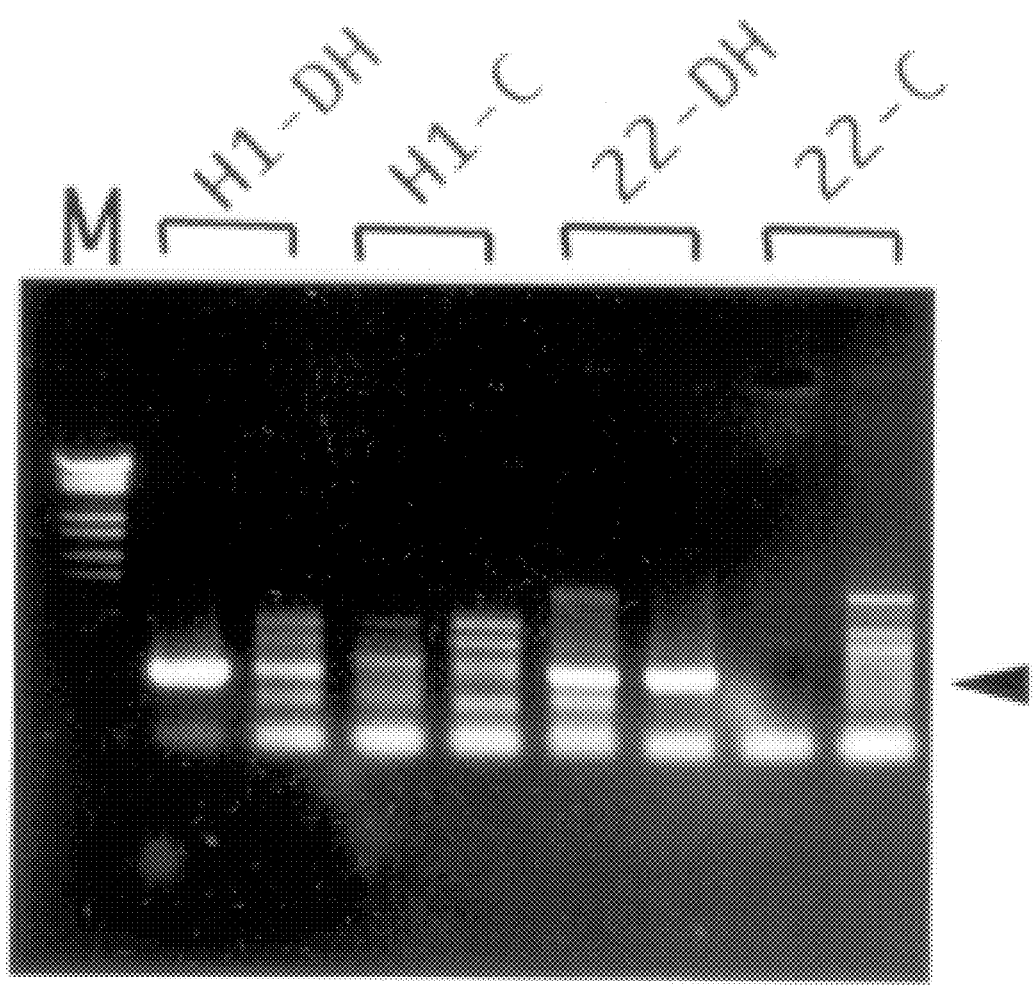
FIG. 9 is a photograph showing the electrophoresis of DNA extracted from transgenic petunia.

The DNA fragments amplified by the above procedure were subjected to electrophoresis. FIG. 9 shows the migration patterns of the fragments. The arrow in this Figure indicates DNA fragments containing the 35S promoter sequence. As shown in FIG. 9, the DNA fragment is detected in H1-DH and 22-DH which are transgenic plants, but not detected in H1-C and 22-C which are non-transgenic plants. Accordingly, transformation of a plant can be confirmed by detecting this DNA fragment.

[EXAMPLE 3]

Virus Inoculation Tests on Transgenic Tobacco

Transgenic tobacco plants were bred for about two to three weeks at room temperature (24–27° C.) after potting and then subjected to a virus inoculation test. Carborundum was sprinkled over tobacco leaves and purified viruses diluted with phosphate buffer were inoculated thereto at a concentration of 1–5 μg/ml by smearing. Then, the leaves were rinsed with water.

When tobacco mosaic virus (TMV) was inoculated to Xanthi nc, the number of local lesions in inoculated leaves was counted three days from the inoculation and was compared to lesions of non-transgenic individuals (control). FIG. 1 shows the appearance of an inoculated leaf from transgenic Xanthi nc tobacco (at the left) and an inoculated leaf from non-transgenic Xanthi nc tobacco (at the right).

When cucumber mosaic virus N-strain (CMV-N) was inoculated to Xanthi nc, the number of local lesions in inoculated leaves was counted four days from the inoculation and was compared to lesions of the control. The results are shown in Table 3.

TABLE 3

Resistance of Transgenic Plants to CMV-N

| | Number of Lesions | |
|---|---|---|
| Strain | Inoculation to a leaf immediately above the largest leaf | Inoculation to the largest leaf |
| SHX-31 | 71 (108) | 48 (79) |
| SHX-32 | 17 (26) | 18 (30) |
| SHX-34 | 14 (21) | 9 (15) |
| SHX-35 | 19 (29) | 6 (10) |
| SHX-36 | 14 (21) | 13 (21) |
| SHX-37 | 20 (30) | 15 (25) |
| SHX-38 | 7 (11) | 10 (16) |
| SHX-33 | 13 (20) | 11 (18) |
| | 7 (11) | 5 (8) |
| SHX-39 | 5 (18) | 4 (7) |
| | 8 (12) | 6 (10) |
| SHX-40 | 16 (24) | 13 (21) |
| | 16 (24) | 10 (16) |
| Control | 66 | 61 |

The inoculation of CMV-N was carried out on two different leaves, i.e., the largest leaf and a leaf immediately above the largest leaf.

With respect to the seven strains of SHX-31, SHX-32, SHX-34, SHX-35, SHX-36, SHX-37 and SHX-38, only one clone individual for each was subjected to the experiment. With respect to the three strains of SHX-33, SHX-39 and SHX-40, two clone individuals for each were subjected to the experiment. With respect to the non-transgenic plant, the number of lesions in five individuals were counted and the mean value was calculated. The figures in parentheses represent the percentage of the number of lesions observed in each strain based on the number of lesions observed in the non-transgenic plant. The difference in values between the transgenic individuals and the non-transgenic individuals was significant in the analysis of variance (ANOVA).

When potato virus Y (PVY) was inoculated to BY-4 and Xanthi nc, the amount of viral growth in upper leaves was assayed by ELISA about two weeks from the inoculation. The results are shown in Table 4.

TABLE 4

Resistance of Transgenic Plants to PVY

| Strain (R_0) | Morphology in Appearance | PVY Concentration (µg/g fresh weight) |
| --- | --- | --- |
| Control | | 4.2 |
| | | 3.7 |
| Individuals developing symptoms (7/10) | | |
| SHB18 | SS | 3.9 |
| SHB19 | SS | 2.8 |
| Individuals developing no symptoms (3/10) | | |
| SHB4 | SS, G, R | 2.1 |
| SHB13 | SS, G, R | 1.2 |
| SHB14 | SS, G, R | 1.4 |

SS: lateral buds, G: delayed aging, R: dwarfing

The values in the Table represent amounts of PVY in plant tissue determined by ELIZA. The difference in value was significant in the analysis of variance (ANOVA).

From the results so far described, the SAHH transgenic organism has been found to be resistant to TMV, CMV and PVY which are the three major viruses causing diseases in tobacco.

[EXAMPLE 4]

Inhibition of SAHH Gene in Yeast

From the above-described Examples, it has been confirmed that various changes are induced in plants by integrating SAHH gene into the plants' genomic genes in such a manner that the gene is expressed in the antisense direction. However, all of those changes described in above Examples are observed at the individual level, i.e., in multicellular systems. Accordingly, there is a possibility that those changes might have been induced by some factor(s) other than the introduction of the antisense gene. Then, in order to determine whether the expression inhibition of SAHH gene is occurring at the cellular level, the following experiment was conducted using Tyl transposon.

Since Tyl transposon of yeast performs replication and particle formation which extremely resemble those of animal retroviruses, model experiments for the study of retroviruses or research and development of antiviral agents (Natsoulis et al., Natung this system (Natsoulis et al., Nature 352, 632).

Propagated Tyl integrates its own sequence into the nuclear DNA of yeast (transposition). When SAHH gene which will be expressed in the antisense direction has been transferred into the yeast in advance, the synthesis of SAHH will be inhibited and, as a result, the frequency of Tyl transposition is thought to decline corresponding to the degree of the above inhibition. Therefore, by examining the frequency of transposition, it is possible to know the degree of the expression inhibition of SAHH gene. The frequency of transposition can be known by introducing into yeast a plasmid containing a Tyl clone and a neomycin-resistant marker gene, culturing the yeast and transferring the yeast to a neomycin-containing medium.

Hereinbelow, the specific procedures of the subject experiment will be described. The subject experiment was conducted according to the method described in "Yeast: A Practical Approach" (Campell et al. (eds.), 1988, IRL PRESS).

Yeast YPH499(a) (Stratagene) was suspended in water to give a cell density of $6\times10^{10}$. Fifty microliters of this suspension was placed in a cuvette with a gap of 0.2 cm and mixed with plasmid pJEF1678 containing a clone of the retrotransposon Tyl and a G418-resistant gene. This plasmid pJEF1678 was released from Dr. Boeke in the United States. The yeast suspension mixed with the plasmid was placed in a chamber of an electroporator (Gene Pulser manufactured by Bio Rad) and a pulse was applied once at 0.6 kV and 25 μF, to thereby introduce plasmid pJEF1678 into yeast YPH499(a).

Subsequently, tobacco SAHH gene was subcloned into yeast plasmid pYEUra3 (Clonetech) at the BamHI-XhoI site so that the gene would be transcribed from gall promoter and expressed in the antisense direction (pYEUra3-TobSAHH). This plasmid was introduced into yeast YPH500 (α) (Stratagene) in a similar manner to that described in the introduction of pJEF1678 into yeast.

The two yeast strains into which a plasmid had been thus introduced were mated in a synthetic minimal galactose medium lacking histidine and uracil. While allowing the two plasmids to coexist, the two strains were cultured at 30° C. for two days. Then, mated yeast cells were cultured in a synthetic minimal glucose medium lacking histidine and uracil at 22° C. for 5–7 days to form colonies. At this time, transposition is induced. Colonies thus formed were transferred to a synthetic minimal glucose medium lacking histidine and uracil, cultured at 30° C. for two days and further cultured in a synthetic liquid glucose medium only lacking uracil at 30° C. overnight. By these treatments, pJEF1678-eliminated cells are generated. The resultant culture broth was diluted with water and seeded in a solid glucose medium only lacking uracil. Cells were cultured at 30° C. for two days. After this cultivation, the yeast was streaked on a synthetic minimal glucose medium only lacking uracil and on a synthetic minimal glucose medium lacking histidine and uracil. By selecting those colonies which did not grow in the latter medium but grew in the former medium, there was selected only the yeast from which plasmid pJEF1678 had been eliminated. The reason why only the plasmid-eliminated yeast was selected here is that resistance to neomycin should be derived from transposition, not from the plasmid.

The yeast selected by the above procedures was streaked on a uracil-lacking glucose medium supplemented with 500 μg/ml of the antibiotic G418. Then, the numbers of G418 resistant colonies and sensitive colonies were counted. As control, yeast YPH499(a) into which pYEUra3 had been introduced instead of pYEUra3-TobSAHH was cultured in a medium containing aristelomycin and the numbers of G418 resistant colonies and sensitive colonies were counted similarly as described above. The results are shown in Table 5.

TABLE 5

Effects of SAHH Inhibition upon Ty1 Transposon

| Aristelomycin Concentration | No. of Resistant Colonies | No. of Sensitive Colonies | Inhibition Ratio |
|---|---|---|---|
| 0 (µg/ml) | 73 | 7 | NA |
| 100 | 66 | 14 | 10 |
| 500 | 50 | 30 | 32 |

| Plasmid Introduced | No. of Resistant Colonies | No. of Sensitive Colonies | Inhibition Ratio |
|---|---|---|---|
| pYEUra3 | 74 | 6 | NA |
| pYEUra3-TobSAHH | 66 | 14 | 12 |

As Table 5 shows, when pYEUra3-TobSAHH was introduced into yeast, an increase in the number of sensitive colonies was observed compared to control. This means that the introduction of the antisense SAHH gene inhibited the transposition of Ty1 transposon into the nuclear DNA. Thus, the fact that the inhibition of expression of SAHH gene has occurred in cells Per se suggests that the SAHH inhibition of the present invention is possible not only in plants illustrated in Examples but also in other organisms such as fungi and animals.

[EXAMPLE 5]

Effects of SAHH upon Endogenous Cytokinins

Figures 6A, 6B:
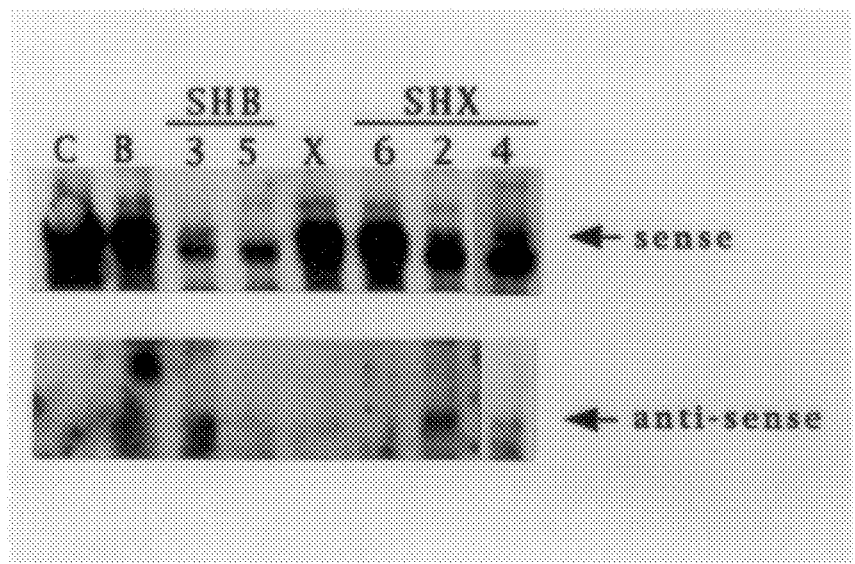
FIGS. 6A and 6B are photographs showing the level of SAHH MRNA extracted from transgenic tobacco.

The expression of antisense SAHH RNA and a reduction in the corresponding sense RNA associated with the expression were analyzed by Northern blotting. Briefly, mRNA was extracted from tobacco leaves and separated with agarose gel. Then, RNA was transferred to a nylon membrane. Subsequently, SAHH mRNA (sense) or antisense RNA was synthesized in vitro. Using these riboprobes, hybridization was performed. The results are shown in FIGS. 6A. and 6B in the Figure represents non-transgenic BY-4 and "X" represents non-transgenic Xanthi nc. Further, "C" represents mRNA extracted from a flower head portion of the control plant. As the Figure shows, the antisense RNA is synthesized in transgenic plants and a reduction in the sense RNA is observed there.

In addition, the amount of endogenous cytokinins in transgenic tobacco was also determined at this time. Briefly, root exudate of tobacco was recovered and medium components were added thereto. Then, a bioassay was conducted on tobacco callus. "A" represents the cytokinin content in transgenic Xanthi nc tobacco and "B" the cytokinin content in non-transgenic Xanthi nc tobacco. "C" represents the cytokinin content when anti-cytokinin was added to the root exudate to thereby suppress the activity of cytokinin. As the Figure shows, the cytokinin content (A) in transgenic tobacco has increased almost three times compared to the cytokinin content (B) in non-transgenic tobacco.

Considering the above results shown in FIGS. 6A–6B and 7, it is presumed that SAHH was reduced by the antisense inhibition of SAHH and as a result, endogeneous cytokinins have been increased.

Effect of the Invention

The present invention provides those organisms in which the expression of SAHH gene is substantially inhibited. Such organisms have excellent properties, such as resistance to viruses, and are industrially useful.

What is claimed is:

1. A transgenic plant in which the expression of S-adenosylhomocysteine hydrolase (SAHH) gene present in its genome is inhibited by inserting all or part of an SAHH gene into the genomic DNA of said plant in a reverse direction such that the reversed SAHH gene induces transcription of an antisense RNA against the endogenous SAHH gene and SAHH enzymatic activity is inhibited.

2. A method for creating a transgenic plant in which the expression of SAHH is inhibited, comprising integrating into the genomic DNA of said plant all or part of an SAHH gene in a reverse direction, such that the reversed SAHH gene induces transcription of an antisense RNA against the endogenous SAHH gene and SAHH enzymatic activity is inhibited.

3. The transgenic plant of claim 1, wherein said plant is a dicotyledon or a monocotyledon.

4. The transgenic plant of claim 1, wherein said plant is an angiosperm or a gymnosperm.

5. The transgenic plant of claim 3, wherein said monocotyledon or dicotyledon is selected from the group consisting of tobacco, tomato, potato, rose, lily, maize and rice.

6. A method of increasing cytokinin concentrations in a plant comprising inhibiting expression of an SAHH gene present in the plant by integrating into the genome of said plant all or part of an SAHH gene inserted in a reverse direction, such that the reversed SAHH gene induces transcription of an antisense RNA against the endogenous SAHH gene and SAHH enzymatic activity is inhibited.

* * * * *